US009694514B2

(12) United States Patent
Vogt

(10) Patent No.: US 9,694,514 B2
(45) Date of Patent: Jul. 4, 2017

(54) DEVICE FOR MIXING AND DISPENSING A PASTY MASS

(71) Applicant: Heraeus Medical GmbH, Wehrheim (DE)

(72) Inventor: Sebastian Vogt, Erfurt (DE)

(73) Assignee: Heraeus Medical GmbH, Wehrheim (DE)

( * ) Notice: Subject to any disclaimer, the term of this patent is extended or adjusted under 35 U.S.C. 154(b) by 121 days.

(21) Appl. No.: 14/066,169

(22) Filed: Oct. 29, 2013

(65) Prior Publication Data

US 2014/0126320 A1 May 8, 2014

(30) Foreign Application Priority Data

Nov. 7, 2012 (DE) .................... 10 2012 021 676
Dec. 18, 2012 (DE) .................... 10 2012 024 710

(51) Int. Cl.
  *B29B 7/80* (2006.01)
  *B01F 11/00* (2006.01)
  (Continued)

(52) U.S. Cl.
  CPC ............ *B29B 7/80* (2013.01); *B01F 11/0054* (2013.01); *B01F 13/0023* (2013.01);
  (Continued)

(58) Field of Classification Search
  CPC ...................................................... B29B 7/80
  See application file for complete search history.

(56) References Cited

U.S. PATENT DOCUMENTS 3,475,010 A * 10/1969 Cook et al. ................... 366/333
4,671,263 A    6/1987 Draenert
(Continued)

FOREIGN PATENT DOCUMENTS

CA     2 708 462 A1   12/2010
CN       1972648 A    5/2007
(Continued)

OTHER PUBLICATIONS

Japanese Office Action, with English-language translation, for corresponding Japanese Application No. 2013-225082 dated Nov. 4, 2014.
(Continued)

*Primary Examiner* — Tony G Soohoo
*Assistant Examiner* — Elizabeth Insler
(74) *Attorney, Agent, or Firm* — Norris McLaughlin & Marcus, P.A.

(57) ABSTRACT

A device, for mixing and dispensing a pasty mass, comprising a cartridge having a mixing element and a feed plunger arranged in it, whereby the mixing element is arranged on a mixing rod, the mixing rod extends through the feed plunger into the inside of the cartridge, the mixing rod and the feed plunger and the cartridge together form a tight connection that seals the cartridge inside of the device with respect to the exterior, whereby the feed plunger is arranged on the mixing rod and such that it can move in the cartridge in axial direction and whereby at least one clamping jaw is arranged on the feed plunger in appropriate manner such that the clamping jaw can be pressed onto the mixing rod by a locking element such that the mixing rod can no longer be shifted with respect to the feed plunger.

25 Claims, 8 Drawing Sheets

Figure 1:
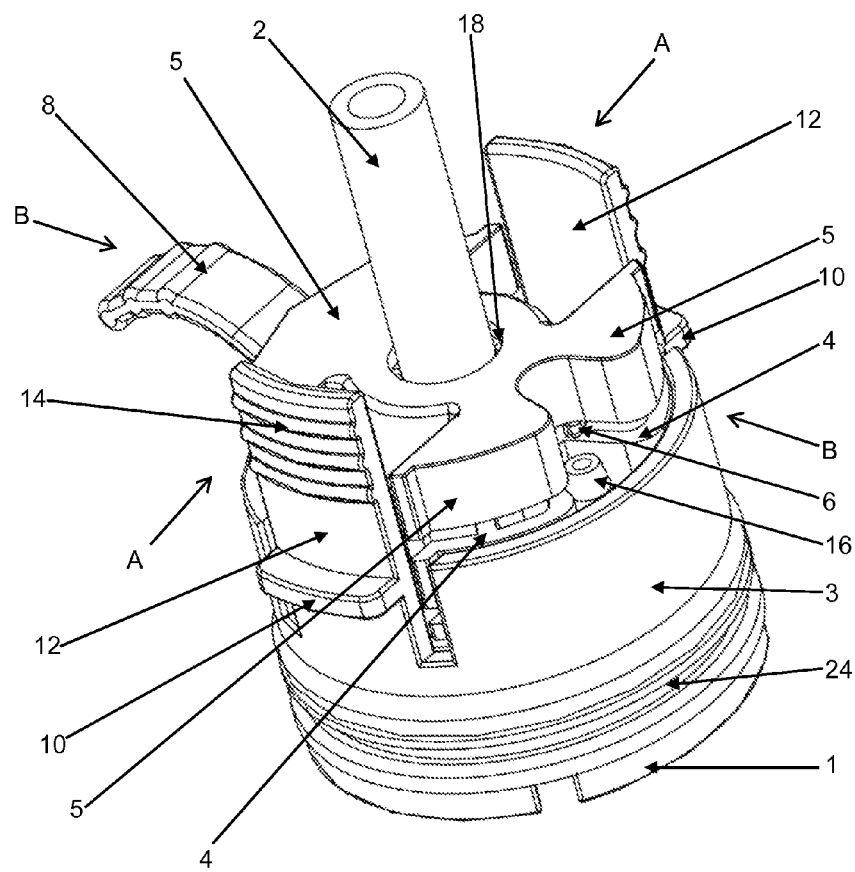

(51) Int. Cl.
    *B01F 13/00* (2006.01)
    *B01F 15/00* (2006.01)
    *B01F 15/02* (2006.01)
(52) U.S. Cl.
    CPC .... *B01F 15/00506* (2013.01); *B01F 15/0226* (2013.01); *B01F 15/0279* (2013.01); *B01F 2215/0029* (2013.01)

(56) References Cited

U.S. PATENT DOCUMENTS

| | | |
|---|---|---|
| 4,973,168 A | 11/1990 | Chan |
| 5,100,241 A | 3/1992 | Chan |
| 5,328,262 A | 7/1994 | Lidgren et al. |
| 5,344,232 A | 9/1994 | Nelson et al. |
| 5,501,520 A | 3/1996 | Lidgren et al. |
| 5,551,778 A | 9/1996 | Hauke et al. |
| 5,586,821 A | 12/1996 | Bonitati et al. |
| 5,624,184 A | 4/1997 | Chan |
| 6,033,105 A | 3/2000 | Barker et al. |
| 7,393,342 B2 | 7/2008 | Henniges et al. |
| 8,297,831 B2 | 10/2012 | Lidgren et al. |
| 2003/0012079 A1 | 1/2003 | Coffeen et al. |
| 2007/0217282 A1* | 9/2007 | Lidgren et al. ............ 366/108 |
| 2010/0046315 A1* | 2/2010 | Merkhan et al. ............ 366/8 |
| 2010/0329074 A1* | 12/2010 | Vogt et al. ............ 366/190 |
| 2012/0132675 A1 | 5/2012 | Vogt et al. |

FOREIGN PATENT DOCUMENTS

| | | |
|---|---|---|
| DE | 36 40 279 A1 | 6/1987 |
| DE | 43 02 230 A1 | 8/1993 |
| DE | 10 2009 031 178 B3 | 9/2010 |
| EP | 0 692 229 A1 | 1/1996 |
| EP | 1 005 901 A2 | 6/2000 |
| EP | 1 016 452 A2 | 7/2000 |
| EP | 1 020 167 A2 | 7/2000 |
| JP | 2007504923 A | 3/2007 |
| JP | 2007275888 A | 10/2007 |
| JP | 2008503317 A | 2/2008 |
| JP | 2011237404 A | 11/2011 |
| WO | 94 26403 A1 | 11/1994 |
| WO | 99 67015 A1 | 12/1999 |
| WO | 2004/100771 A2 | 11/2004 |
| WO | 2005/048886 A2 | 6/2005 |
| WO | 2009 105905 A1 | 9/2009 |

OTHER PUBLICATIONS

Canadian Office Action for corresponding Canadian Application No. 2,830,629 dated Nov. 17, 2014.
Australian Office Action for corresponding Australian Application No. 2013254886 dated Nov. 27, 2014.
Japanese Office Action, with English-language translation, for corresponding Japanese Application No. 2013-225082 dated Jan. 27, 2015.
German Office Action from corresponding application DE 10 2012 024 710.9 issued Jul. 12, 2013.
Chinese Office Action, with English-language translation, for corresponding Chinese Application No. 201310669792.7 dated Jun. 1, 2015.
Chinese Office Action, with English-language translation, for corresponding Chinese Application No. 201310669792.7 dated Feb. 1, 2016.

* cited by examiner

DEVICE FOR MIXING AND DISPENSING A PASTY MASS

The invention relates to a device for mixing and dispensing a pasty mass, in particular a bone cement. Moreover, the invention relates to a bone cement system comprising a device of this type and a method for producing a cement mixture, in particular of a bone cement, having a device of this type or a bone cement system of this type.

Polymethylmethacrylate (PMMA) bone cements are based on the pioneering work of Sir Charnley. PMMA bone cements consist of a liquid monomer component and a powder component. The monomer component generally contains the monomer, methylmethacrylate, and an activator (N,N-dimethyl-p-toluidine) dissolved therein. The powder component, also called bone cement powder, comprises one or more polymers that are produced through polymerisation, preferably suspension polymerisation, based on methylmethacrylate and co-monomers, such as styrene, methylacrylate or similar monomers, a radiopaquer, and the initiator, dibenzoylperoxide. Mixing the powder component and the monomer component, swelling of the polymers of the powder component in the methylmethacrylate generates a dough that can be shaped plastically and is the actual bone cement. Mixing the powder component and the monomer component, the activator, N,N-dimethyl-p-toluidine, reacts with dibenzoylperoxide while forming radicals. The radicals thus formed trigger the radical polymerisation of the methylmethacrylate. Upon advancing polymerisation of the methylmethacrylate, the viscosity of the cement dough increases until the cement dough solidifies.

Polymethylmethacrylate bone cements can be mixed by mixing the cement powder and the monomer liquid in suitable mixing beakers with the aid of spatulas. This procedure is disadvantageous in that air inclusions may be present in the cement dough thus formed and cause destabilisation of the bone cement later on. For this reason, it is preferred to mix bone cement powder and monomer liquid in vacuum mixing systems, since mixing in a vacuum removes air inclusions from the cement dough to a large extent and thus achieves optimal cement quality. Bone cements mixed in a vacuum have clearly reduced porosity and thus show improved mechanical properties. A large number of vacuum cementing systems have been disclosed of which the following shall be listed for exemplary purposes: U.S. Pat. No. 6,033,105 A, U.S. Pat. No. 5,624,184 A, U.S. Pat. No. 4,671,263 A, U.S. Pat. No. 4,973,168 A, U.S. Pat. No. 5,100,241 A, WO 99/67015 A1, EP 1 020 167 A2, U.S. Pat. No. 5,586,821A, EP 1 016 452 A2, DE 36 40 279 A1, WO 94/26403 A1, EP 1 005 901A2, U.S. Pat. No. 5,344,232 A.

Cementing systems are a development, in which both the cement powder and the monomer liquid are already pre-packaged in separate compartments of the mixing systems and are mixed with each other in the cementing system only right before application of the cement, such as proposed in EP 0 692 229 A1. One essential problem of these systems is the sterilisation of the entire system including the cement powder and the previously sterile filtered monomer liquid. A particular problem is the implementation of ethylene oxide sterilisation, which is used commonly for bone cements. This sterilisation method is advantageous as compared to sterilisation by gamma radiation in that the polymers present in the cement powder are not degraded and the cement properties remain unaffected by the ethylene oxide sterilisation. One problem associated with the sterilisation with ethylene oxide is that the gaseous agent first needs to penetrate into the cartridge and/or the cement reservoir and thus into the cement powder and needs to diffuse from the cartridge after the sterilisation is completed. For this reason, it is necessary that the gas exchange between the interior of the cartridge and/or of the reservoir and the surroundings is basically unimpeded. In contrast, the mixing system that is ready for use needs to be sealed sufficiently tightly to allow the cement to be mixed in a vacuum.

Commercially available mixing system resolve this contradiction in that a lid having a porous disc is screwed onto the cartridge and needs to be removed right before the application of cement. Rather than said lid, a vacuum-tight cartridge head containing a mixing device, a vacuum connector, and an opening for the dispensing tube to be attached later is screwed on. The medical user therefore needs to open the cementing system right before mixing the cement, and then re-close it. This allows germs, etc., to reach the previously sterilised bone cement powder.

DE 10 2009 031 178 B3 proposes a device for mixing and dispensing bone cement that was implemented in the Palacos® PRO cementing system, in which a gas-permeable sterilisation plunger and a sealing plunger are arranged such as to be axially mobile on a mixing rod. The sterilisation plunger in the sterilisation position closes the cartridge appropriately such that no cement powder can exit, while a gas-permeable exchange surface of the sterilisation plunger allows ethylene oxide to flow into the cartridge for sterilisation of the cement powder and of the inside of the cartridge and to diffuse out of the interior space of the cartridge after the sterilisation is completed. The sterilisation plunger contains a circumferential groove that is engaged by a circumferential fin of the cartridge that is arranged on the inside of the cartridge. By this means, the sterilisation plunger is reversibly connected to the cartridge and the sterilisation plunger is affixed.

The sealing plunger is plugged onto and/or into the sterilisation plunger before the bone cement is mixed. This forms a plunger that consists of two parts. Similar to a method according to the invention, a vacuum is applied then to the sealing plunger and the monomer transfer from the monomer reservoir into the inside of the cartridge to the cement powder situated therein is started through actuation of an opening mechanism. Subsequently, the cement powder is mixed with the monomer liquid by means of the mixing rod and a mixing element situated thereon. Subsequently, no further vacuum is drawn. The mixing rod is pulled towards the two-part plunger until the mixing element touches against the underside of the two-part plunger. Then, the mixing rod is broken off at a pre-determined breakage site right above the top of the two-part plunger. The cartridge containing the ready-made cement dough is then detached from the foot part. Then, a dispensing tube is attached to the cartridge head and the cartridge is connected to a dispensing device.

During the first motion of the pestle of the dispensing device onto the two-part plunger, the groove-fin connection of the sterilisation plunger and cartridge is detached by travelling over the fin of the cartridge and the two-part plunger can then be shifted axially towards the cartridge head. The cartridge is being held approximately vertical and the dispensing device presses the two-part plunger axially towards the cartridge head, whereby the air present in the cartridge exits through the dispensing tube until the cement dough reaches the dispensing tube. After this follows the application of the cement dough.

DE 43 02 230 A1 discloses a mixing device for bone cement, in which a vacuum connector is present on the cartridge head and which possesses a reversibly affixed plunger on the cartridge end. Once the powder component and the monomer liquid are mixed, the plunger affixed by means of a turn-lock fastener is detached by means of a rotary motion of the cartridge with respect to the plunger. For this purpose, the plunger is provided with recesses on its outside by means of which the plunger can engage beading of a special blister and thus is affixed when the cartridge rotates about its longitudinal axis. Thus detached, the plunger is moved, by the action of the vacuum applied to it, towards the cartridge head and collects the cement dough during this motion and transports it to the cartridge head.

The mixing device disclosed in DE 10 2009 031 178 B3 does not allow the mixed cement dough to be collected in a vacuum by moving the plunger towards the cartridge head. A collecting in a vacuum cannot proceed since, firstly, the fixation of the sterilisation plunger on the cartridge can be detached only through the action of the pestle of the cement applicator, whereas manual unlocking is not feasible, and, secondly, since the broken off mixing rod would be aspirated into the inside of the cartridge upon the action of a vacuum.

It is therefore the object of the invention to overcome the disadvantages of the prior art based on DE 10 2009 031 178 B3, i.e. to develop a mixing device that overcomes the above-described issues of the mixing device disclosed in DE 10 2009 031 178 B3 and further disadvantages that are not specified above, but result directly from the prior art. In particular, the invention is to provide a mixing device that is a closed mixing device such that neither the monomer nor the cement powder directly contact the surroundings before and during the mixing process such that the cement components cannot become contaminated. The mixing device is to possess a plunger that can be moved towards the cartridge head upon the action of a vacuum after the cement components have been mixed in the cartridge, whereby the cement dough formed is collected and moved towards the cartridge head. Moreover, the mixing rod is not to be aspirated into the inside of the cartridge due to the action of the vacuum, while the cement dough is collected.

The objects of the invention are met by a device for mixing and dispensing a pasty mass, in particular a bone cement, comprising a cartridge that is open or can be opened on two ends and has a mixing element and a feed plunger arranged in it, whereby the feed plunger, in a starting position, is arranged in the region of a first cartridge end, the mixing element is arranged on a mixing rod, the mixing rod extends through the feed plunger into the inside of the cartridge, the mixing rod and the feed plunger and the cartridge together form a tight connection that seals the cartridge inside of the device with respect to the exterior, whereby the feed plunger is arranged such as to be axially mobile on the mixing rod and in the cartridge, and whereby at least one clamping jaw is arranged on the feed plunger in appropriate manner such that the clamping jaw can be pressed onto the mixing rod by means of a locking element such that the mixing rod can no longer be shifted with respect to the feed plunger.

According to the invention, the clamping jaw preferably forms an two-dimensional connection to the mixing rod. The clamping surface can be toothed in this context. Alternatively, the clamping jaw can just as well be designed as mandrel or having an edge, which, when pressed onto the mixing rod, are pressed into the surface of the mixing rod. Basically, it is conceivable just as well that the clamping jaw is designed as a belt that clamps or ties the mixing rod to the feed plunger when it is tied up.

The mixing rod no longer being shiftable does not mean that it could not be shifted through an unexpected action of force, but rather that it can no longer be shifted with respect to the feed plunger during normal use of the device. In particular, the mixing rod is to no longer be shiftable on the inside of the cartridge with respect to the feed plunger due to the action of a vacuum.

According to the invention, the axial direction shall be understood to mean the direction, in which the mixing rod can be shifted and which forms a symmetry axis of the internal wall of the cartridge or of (at least essentially) the entire cartridge. According to the invention, the internal cartridge walls are preferably cylindrical, preferably the cartridge is cylindrical. In this case, the cylinder axis of the cartridge or of its internal cartridge walls preferably coincides with the axis to which the axial direction refers.

The invention can provide the clamping jaw or at least one of the clamping jaws to comprise a snap-in hook that snaps into a counter-snap-in means on the locking element when the locking element is or is being slid or plugged onto the clamping jaws.

The invention can preferably provide the mixing element to be arranged more deeply inside the cartridge than the feed plunger in its starting position. The starting position of the feed plunger is the position, in which the pasty mass is not yet squeezed from the inside of the cartridge. The invention can just as well provide the mixing element to be arranged in front of the side of the feed plunger, towards which the feed plunger is moved in order to squeeze the pasty mass from the interior of the cartridge. Said direction is referred as the direction facing inwards (towards the inside of the cartridge). The opposite direction is referred to as the direction facing outward with respect to the feed plunger.

According to a development, the invention can just as well provide the locking element to be a part of the feed plunger, preferably a separate part of the feed plunger, that can be shifted on the mixing rod in axial direction with respect to the remaining feed plunger and, upon the locking element being slid or plugged together with the remaining feed plunger, to press the at least one clamping jaw onto the mixing rod such that the mixing rod can no longer be shifted with respect to the feed plunger.

This structure is inexpensive and easy to implement. Moreover, this structure allows for easy operation of the device.

A particularly preferred development of the invention proposes to arrange between the locking element and the remaining feed plunger a manually-removable spacer as securing element that prevents the locking element and the remaining feed plunger from being slid together or plugged together inadvertently.

The spacer prevents, in inexpensive and easily implemented manner, inadvertent locking of the mixing rod to the feed plunger and thus prevents incorrect operation of the device in the often hectic application scenarios, for example during a surgery.

Moreover, the invention preferably provides the locking element to be arranged on the outward-facing end of the feed plunger.

This simplifies both the operation and the structure of the device.

According to a development, the invention can provide the locking element to be connectible to the feed plunger by sliding together or plugging it onto the remaining feed plunger in a positive fit- or non-positive fit-like manner, in particular to be connectible to the sealing plunger of the feed plunger in appropriate manner such that the at least one clamping jaw is pressed onto the mixing rod. Moreover, the invention can provide the locking element to be connectible to the sealing plunger in non-detachable manner by means of at least one snap-in element.

The invention can just as well provide the feed plunger to comprise, on the end facing the inside of the cartridge, a sterilisation plunger adjacent to which the mixing element is arranged in the cartridge, whereby the sterilisation plunger comprises at least one gas-permeable exchange surface and preferably is or can be connected to the cartridge by means of at least one detachable snap-in element.

Having the sterilisation plunger allows for disinfection of the inside of the cartridge with a sterilising gas, such as ethylene oxide. This is of central importance, especially for clinical application.

Moreover, the invention can provide the feed plunger to comprise a sealing plunger, in particular as a separate part of the remaining feed plunger, whereby the sealing plunger is arranged such that it can be shifted axially on the mixing rod and has at least one clamping jaw arranged on it.

The central task of the sealing plunger is to seal the cartridge in one direction and to also ensure that the content of the cartridge (the pasty mass), being squeezed out, cannot inadvertently escape past the sealing plunger against the direction of squeezing. The proposed separate or modular structure of the feed plunger provides an inexpensive and simple way of implementing the structure according to the invention.

Devices according to the invention having sterilisation plunger and sealing plunger can be provided such that the sterilisation plunger and the sealing plunger and the locking element, slid together or plugged together, form an at least two-part feed plunger, preferably together with the locking element form an at least three-part feed plunger.

Said modular structure of the feed plunger enables the use of parts that are simple and thus inexpensive to fabricate. Moreover, the simple structure reduces the risk of malfunction.

In this context, the invention can just as well provide that the sealing plunger can be plugged onto the sterilisation plunger and that the locking element can be plugged or slid onto the feed plunger part assembled from the sealing plunger and the sterilisation plunger, while forming a three-part feed plunger.

Said structure is particularly simple and easy to use.

A development of the invention proposes the remaining feed plunger, in particular the sealing plunger, to comprise at least one recess on the outside for accommodating a handle part of the at least one snap-in means of the sterilisation plunger.

The recess allows the device to be operated manually, for example by means of two fingers, while keeping the structure of the device both compact and space-saving.

The invention can preferably provide the sterilisation plunger and/or the sealing plunger to be a separate part from the remaining feed plunger.

The separate parts are easier and less expensive to fabricate as compared to the parts being connected to each other. However, the parts of the multi-part feed plunger can just as well be firmly connected to each other by means of flexible connections with significantly limiting the functionality for the purposes of the present invention.

The invention can just as well provide the three-part feed plunger system to surround the mixing rod.

According to a particularly preferred development, the invention can provide the feed plunger, in particular the three-part feed plunger system, to be axially shiftable into the cartridge, in particular into a mixing cylinder of the cartridge, after an unlocking by means of a pressure in order to move a bone cement dough prepared by mixing bone cement powder and a monomer from the inside of the cartridge towards a cartridge head that is arranged on a second end of the cartridge that is opposite from a first end of the cartridge and includes the second opening.

By this means, the three-part feed plunger can be used as feed plunger for pasty masses.

In this context, the invention can provide the dispensing opening in the cartridge head to comprise a connecting means, in particular a connecting thread.

The invention can just as well provide the mixing rod to comprise a pre-determined breakage site, whereby the pre-determined breakage site of the mixing rod preferably is arranged appropriately such that the predetermined breakage site is covered by the spacer when the mixing element including the mixing rod is pulled to the end of the feed plunger facing into the inside of the cartridge.

Having the predetermined breakage site ensures that the mixing rod breaks off reproducibly and thus permits for reliable operation of the device. Having the pre-determined breakage site covered by the spacer prevents the mixing rod from breaking off inadvertently since the spacer supports the predetermined breakage site and torques that may be present would act further outwards on the mixing rod on which the mixing rod is guided out of the feed plunger. The predetermined breakage site is exposed and the mixing rod becomes easily breakable at that site only after the spacer is removed and, possibly, after the locking element is pressed in or plugged in.

The invention can just as well provide the feed plunger, in particular the sealing plunger and/or the sterilisation plunger, to comprise at least one vacuum connector that provides a connection from outside through the feed plunger into the inside of the cartridge.

The vacuum connector can be used to remove a sterilising gas from the cartridge, to aspirate a fluid component of the pasty mixture into the cartridge, and to propel the feed plunger into the inside of the cartridge.

A preferred embodiment of the device according to the invention having a vacuum connector proposes to have a non-return valve arranged in the vacuum connector.

A development of the invention proposes to arrange the at least one clamping jaw on the feed plunger, in particular on the sealing plunger, such as to be tiltable and that it can be pressed onto the mixing rod, by its end or ends facing away from the bottom of the feed plunger by tilting in the direction of the longitudinal axis of the mixing rod.

Moreover, the invention can provide the locking element to comprise at least one tiltable clamping jaw that can be pressed onto the mixing rod, by its end end facing away from the pivot point of the clamping jaw by tilting in the direction of the longitudinal axis of the mixing rod.

Clamping jaws of said structure can be implemented inexpensively and are also robust and thus allow for reliable operation of the device.

Moreover, the invention proposes that the locking element and/or the sealing plunger comprise at least one element capable of elastic deformation which presses the at least one clamping jaw onto the mixing rod after the locking element is slid together or plugged onto the remaining feed plunger, in particular the sealing plunger.

The elastic element provides a secure connection of the clamping jaw to the mixing rod.

The objects of the invention are also met by a bone cement system comprising a device of said type, a reservoir element for a binding agent, in particular a monomer, and a base element, whereby the base element stores and connects the device and the reservoir element.

The bone cement system possesses all components for providing a bone cement.

In this context, the invention can provide the base element to comprise a coupling means for a non-positive fit- or positive fit-like connection to the device, in particular a non-positive fit- or positive fit-like connection to the dispensing opening of the device.

The device is thus easy to insert into the bone cement system.

Moreover, the invention can provide the reservoir element to comprise a valve means, in particular a valve means for manual operation, in order to control and/or trigger a flow of monomer from the reservoir element.

This allows the flow of bone cement from the bone cement system to be controlled.

Moreover, bone cement systems according to the invention can provide the base element to comprise a conduit, whereby the conduit connects the reservoir element to the inside of the cartridge such that the monomer can flow from the reservoir element through the conduit into the cartridge.

The bone cement system is then well-suited for producing the bone cement mixture.

Bone cement systems according to the invention can also provide the reservoir element to store a reservoir container for the binding agent, whereby it can be preferred that the reservoir container is a glass container.

The glass container is chemically resistant to the binding agent and can be opened easily by breaking it.

The objects on which the invention is based are also met through a method for producing a cement mixture, in particular of a bone cement, having a device of this type or a bone cement system of this type that includes the following procedural steps in the order given:
A) providing a cartridge at least regions of which are filled with a powder;
D) filling the cartridge with a fluid, preferably with a binding agent, particularly preferably with a monomer;
E) mixing the powder by means of the mixing element;
F) locking the mixing rod in the feed plunger by means of the at least one clamping jaw; and
H) dispensing the cement mixture through propelling the feed plunger.

Furthermore, an additional procedural step B) can be provided:
B) filling a sterilising gas through the gas-permeable exchange surface and sterilising the interior space of the cartridge and the powder after step A) and before step D).

Moreover, the invention can provide the cartridge to be closed by means of the sterilisation plunger in step A).

These measures allow a sterile cement and/or a sterile pasty mass to be provided.

Methods according to the invention can also be developed further by means of a step C) plugging the sealing plunger into the sterilisation plunger after step B) and before step D).

Moreover, a step G) of breaking-off the mixing rod locked by means of the at least one clamping jaw can be provided after step F) and before step H), whereby the mixing rod preferably is broken off at a predetermined breakage site.

According to a development, the method according to the invention can provide the mixing rod in step F) to be locked by sliding or plugging the locking element onto the remaining feed plunger, in particular onto the sealing plunger, whereby the locking element presses the at least one clamping jaw onto the mixing rod due to the sliding or plugging.

In this context, the invention can provide the spacer as a securing element to be removed before the sliding or plugging of the locking element in step F).

Finally, the invention can just as well provide the feed plunger, in particular the multi-part feed plunger, is detached from the cartridge in step H) through detaching the at least one snap-in element before dispensing the cement mixture.

The invention is based on the surprising finding that the use of a clamping jaw or an equivalent clamping device, which, according to the invention, can also be considered to be a clamping jaw, allows to provide a device in which a mixture can be mixed by means of a mixing element in a cartridge with the aid of a mixing rod, whereby the mixing rod, when it is not needed any longer for a further use of the device and would be rather cumbersome, can be broken off easily and reproducibly without adverse effect on the functionality of the device.

An inexpensive and easily operated device can be implemented, in particular, if the feed plunger has a multi-part structure.

The mixing device has a feed plunger that can be unlocked manually and can be moved in the cartridge towards the cartridge head upon the action of a vacuum after the cement components have been mixed, whereby the cement dough formed (the pasty mass) is collected and moved towards the cartridge head. The mixing device is designed appropriately such that, after mixing is completed, the mixing rod to be broken off can be placed against the feed plunger in affixed manner such that the same cannot be aspirated into the inside of the cartridge due to the vacuum effect when the cement dough is collected in a vacuum.

The objects of the invention are met by a device for mixing and dispensing bone cement, having a cylinder-shaped cartridge, in which a mixing element is arranged, whereby the mixing element is axially mobile by means of a mixing rod that is guided out of a first cartridge end in sealed manner, and having a sealing plunger that closes the cartridge in gas-tight manner and is arranged in the region of the first cartridge end and is axially mobile on the mixing rod, whereby
a) a sterilisation plunger is arranged in the region of the first cylinder end between the mixing element and the sealing plunger, and possesses at least one gas-permeable exchange surface and is connected reversibly to the cartridge by means of at least one snap-in element that can be detached manually from outside;
b) the sealing plunger, which is axially shiftable separately from the sterilisation plunger, is arranged on the mixing rod;
c) at least one clamping jaw is arranged on the sealing plunger and/or on a separate locking element in appropriate manner such that the clamping jaw can be pressed against the mixing rod;
d) a locking element is arranged that can be shifted axially on the mixing rod and when slid together with the sealing plunger presses the at least one clamping jaw against the mixing rod in appropriate manner such that the same can no longer be shifted by the action of a vacuum; and
whereby the sterilisation plunger and the sealing plunger and the locking element form a three-part feed plunger after they are slid or plugged together.

The workings of the device according to the invention are explained in more detail in the following. The sterilisation plunger is situated in the cartridge right next to the cartridge bottom and is affixed on the inside of the cartridge by means of the snap-in means. A recess of the sterilisation plunger has the mixing rod situated in it, whereby the mixing rod can be moved axially through the recess. A mixing element is arranged at the end of the mixing rod that is situated on the inside of the cartridge. Preferably, mixing vanes can be used as mixing elements. A handle is arranged on the external end of the mixing rod. The sterilisation plunger contains a gas-permeable exchange surface. A sealing plunger and a locking element, which each are arranged such as to be axially mobile about the mixing rod, are situated separate from the sterilisation plunger.

In the sterilisation position, the sterilisation plunger is separated from the sealing plunger and the locking element, whereby the sterilisation plunger is the only such element that is already inserted into the cartridge and snapped-in into the cartridge. The gaseous sterilisation means (for example and preferably ethylene oxide) can enter through the gas-permeable exchange surface into the inside of the cartridge and sterilise the cement powder situated therein as well as the inside of the cartridge. Then, the sterilisation means diffuses through the gas-permeable exchange surface and out of the cartridge. For this degassing process to proceed in an economically reasonable amount of time, the exchange surface must be sufficiently large. Preferably, the exchange surface accounts for at least 25%, particularly preferably at least 40%, even more particularly preferably at least 50%, of the cross-sectional area of the cartridge.

Producing a medical cement, in particular a bone cement, the cartridge can be provided as a cement cartridge, i.e. can be provided as a cartridge that has sufficient stability to allow pasty cement to be mixed inside it and to be dispensed from the cement cartridge. Moreover, the cartridge must be chemically resistant to a sufficient degree such that no interfering substances are dissolved out of the walls of the cement cartridge. This is very important, in particular with regard to cement cartridges for cements for medical applications, such as bone cements.

In order to prepare the cement by mixing, the sealing plunger is slid or plugged onto, or into as the case may be, the sterilisation plunger such that the cartridge is closed off from the surrounding atmosphere in gas-tight manner and such that the recesses of the sealing plunger accommodate the grasping parts of the sterilisation plunger. The sealing plunger contains a vacuum connector that is connected to the inside of the cartridge in gas-permeable manner. Only then, the interior space of the cartridge is evacuated by means of a vacuum hose using the vacuum connector. Then, the monomer is transferred from a reservoir container to the cartridge by the effect of a vacuum. For example, the monomer is aspirated by means of the vacuum. Then, in the presence of a vacuum, the mixing element situated on the mixing rod is used to mix the cement components until a homogeneous cement dough is produced. Subsequently, the mixing rod is pulled upwards towards the sterilisation plunger until the mixing element touches against the underside of the sterilisation plunger. The vacuum is then turned off briefly. Then the locking element is slid or pressed by hand onto the sealing plunger. The locking element presses the clamping jaw or clamping jaws against the mixing rod and the mixing rod is affixed through the at least one clamping jaw. Then, the upper part of the mixing rod is broken off using the predetermined breakage site. Then the vacuum is applied again and the at least one grasping part is moved in the direction of the longitudinal axis of the cartridge. This detaches the snap-in element from the inside of the cartridge and the entire plunger, containing the sterilisation plunger and the sealing plunger, moves towards the cartridge head due to the action of the vacuum, whereby the previously mixed cement dough is collected and moved along towards the cartridge head. Then the vacuum hose is pulled off and the cartridge is ready for cement application.

The entire device can preferably be made from plastic materials, whereby thermoplastic materials can be used in particularly cost-efficient manner and are thus preferred according to the invention. Said plastic materials can be used to fabricate the device according to the invention through conventional plastic injection moulding.

Figure 2:
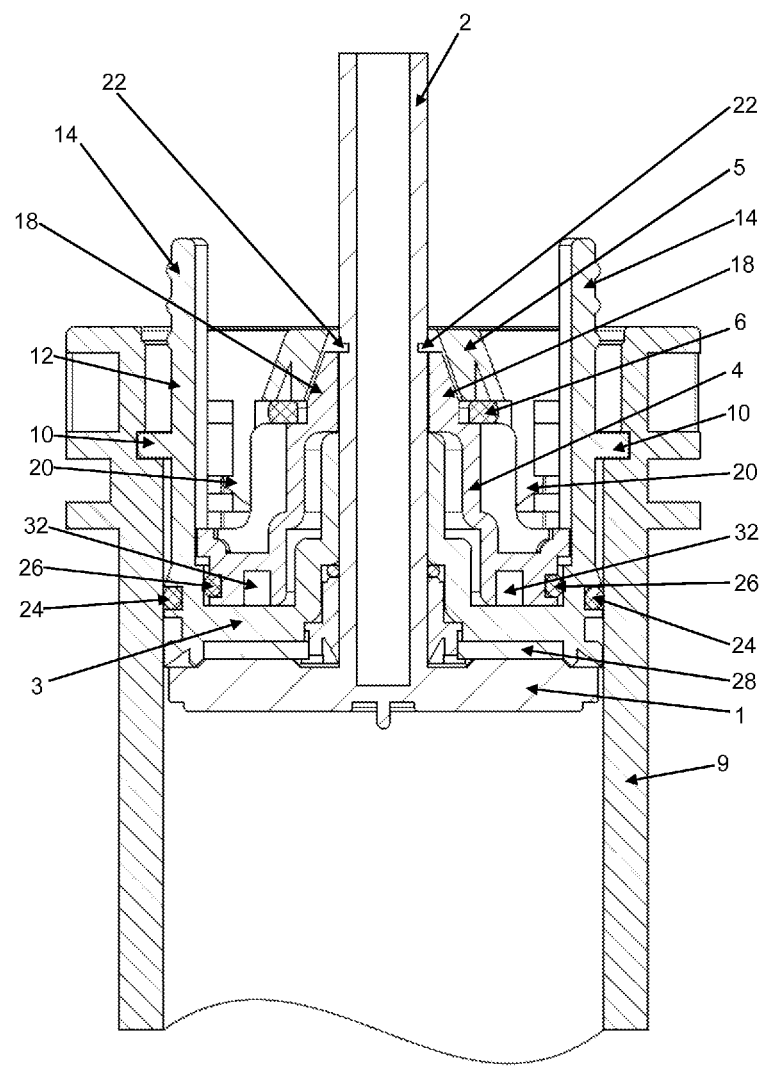
Figure 3:
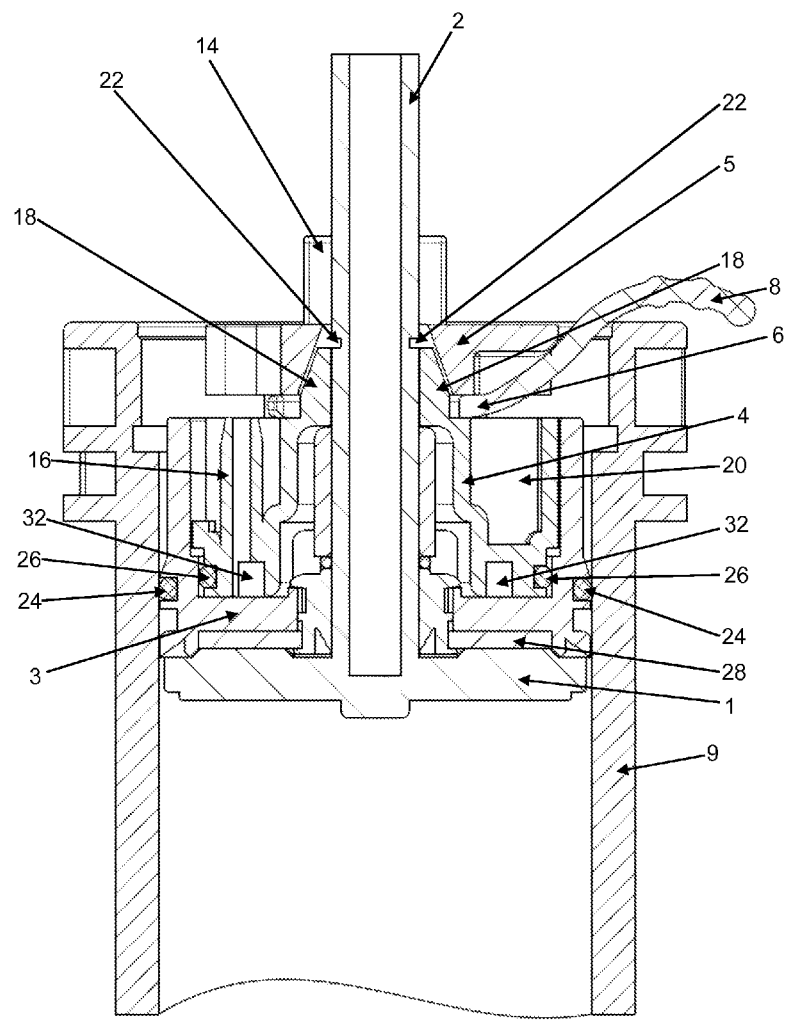
Figure 4:
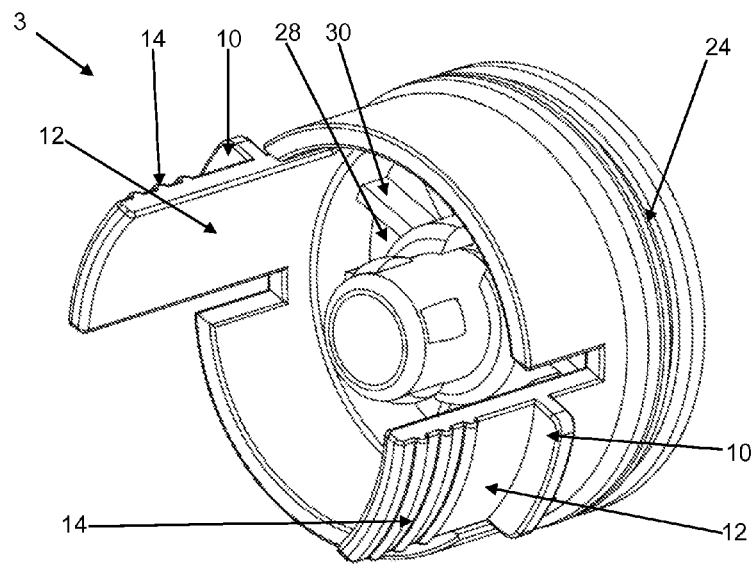
Figure 5:
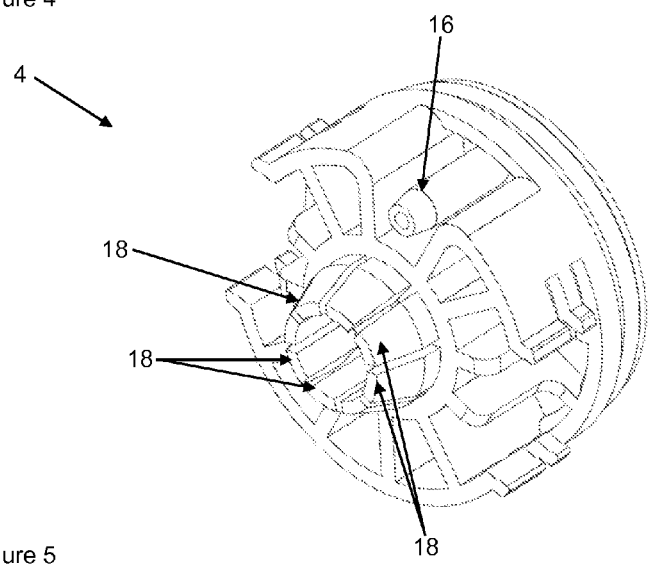
Figure 6:
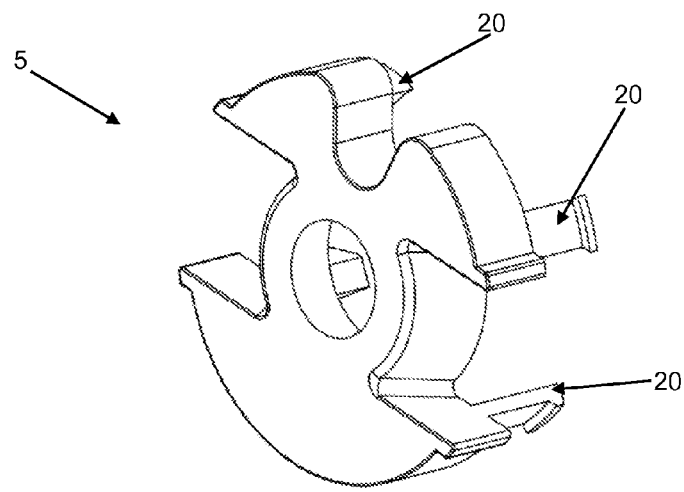
Figure 7:
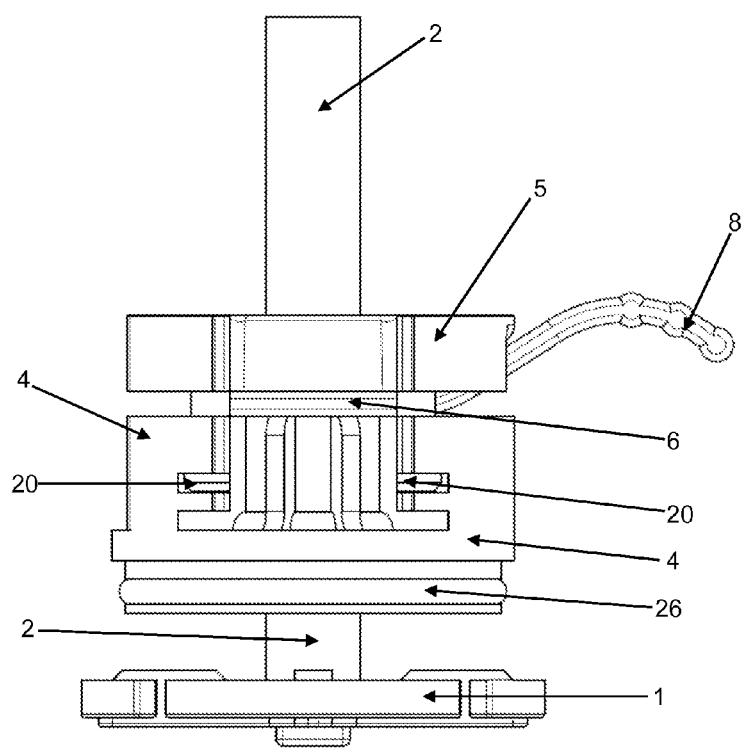
Figure 8:
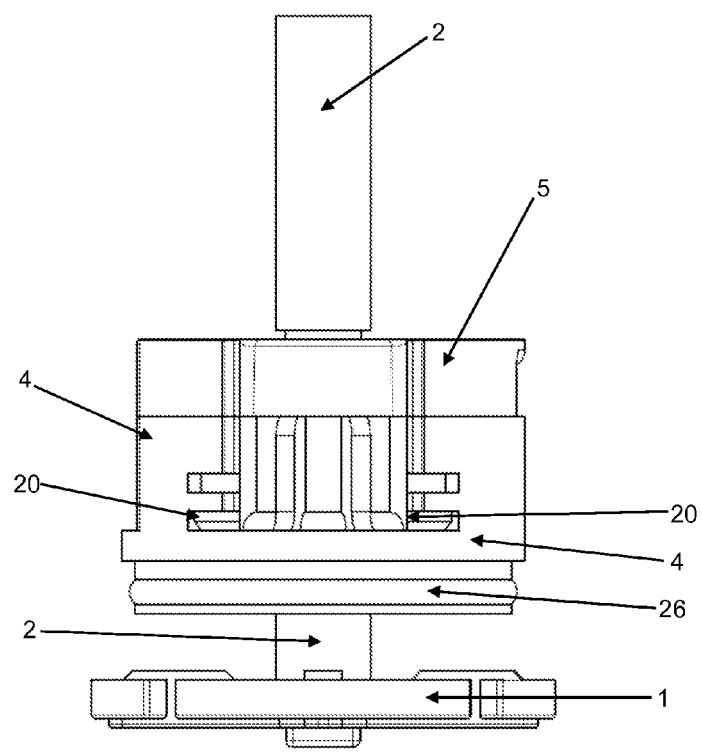
Figure 9:
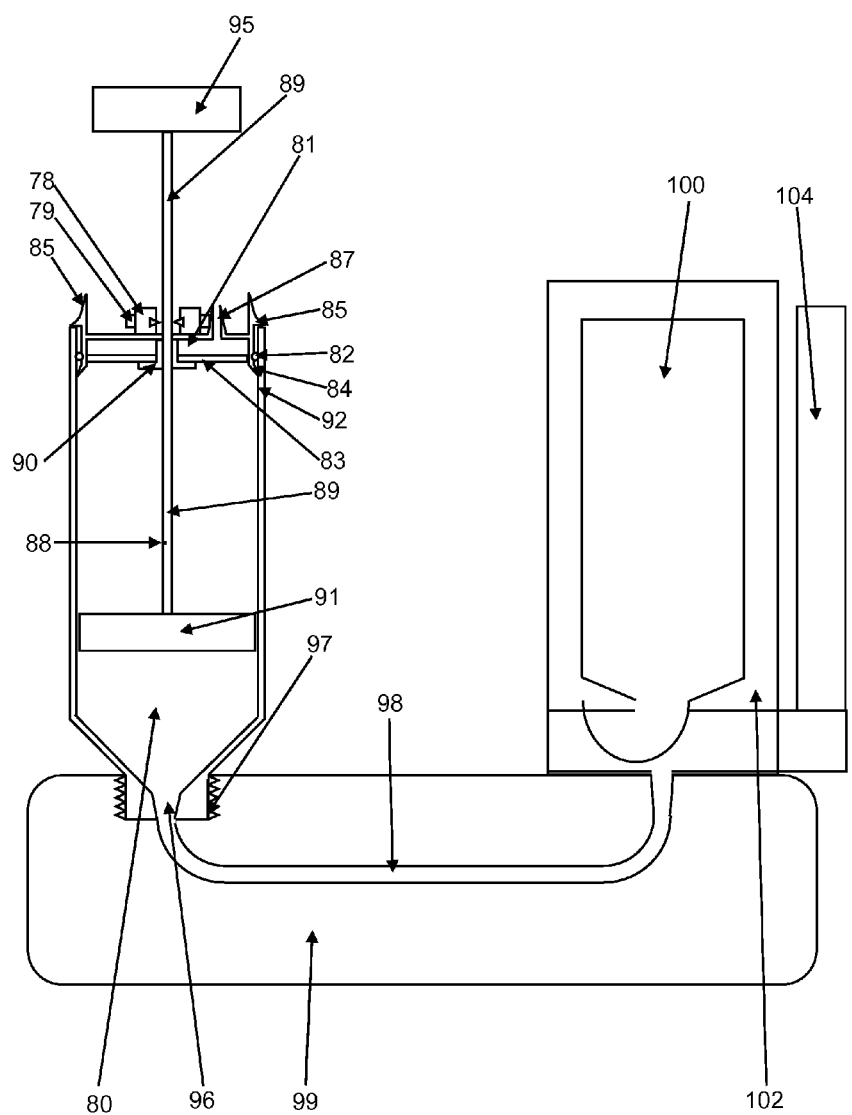

Exemplary embodiments of the invention shall be illustrated in the following on the basis of nine schematic figures, though without limiting the scope of the invention. In the figures:

FIG. 1: shows a schematic perspective view of a feed plunger having a mixing element and a mixing rod for a device according to the invention;

FIG. 2: shows a cross-sectional view through a device according to the invention;

FIG. 3: shows a cross-sectional view through a device according to the invention perpendicular to the view of FIG. 2;

FIG. 4: shows a schematic perspective view of a sterilisation plunger for a device according to the invention;

FIG. 5: shows a schematic perspective view of a sealing plunger for a device according to the invention;

FIG. 6: shows a schematic perspective view of a locking element for a device according to the invention;

FIG. 7: shows a schematic side view of a feed plunger having a securing element and non-locked mixing rod;

FIG. 8: shows a schematic side view of a feed plunger having no securing element and a locked mixing rod; and FIG. 9: shows a schematic cross-sectional view of a bone cement system according to the invention.

FIG. 1 shows a schematic perspective view of a feed plunger having a mixing element 1 and a mixing rod 2 for a device according to the invention. The feed plunger has cylindrical outer dimensions and is intended to be inserted into a cartridge (not shown) having a cylindrical internal wall. The feed plunger is made up of three separate parts. In the assembled state, the mixing element 1 is arranged on the inside of the cartridge and serves for mixing the cartridge content. For this purpose, the mixing element 1 can be moved over the mixing rod 2 in longitudinal direction of the cartridge and can be rotated about the mixing rod 2 as the rotation axis.

The feed plunger comprises an external sterilisation plunger 3 that forms the part of the feed plunger that is adjacent to the mixing element 1. The sterilisation plunger 3 is arranged on the top of the mixing element 1. The sterilisation plunger 3 is shown separately in FIG. 4. A sealing plunger 4 is arranged in and on the sterilisation plunger 3 as second part of the feed plunger. The sealing plunger 4 is shown separately in FIG. 5. A locking element 5 is arranged above the sealing plunger 4 as third part of the feed plunger. The locking element 5 is shown separately in FIG. 6.

Whenever details of the sterilisation plunger 3, sealing plunger 4, and locking element 5 are discussed hereinafter, reference shall be made also to FIGS. 4, 5, and 6.

A spacer 6 is arranged as securing element 6 between the sealing plunger 4 and the locking element 5 and is used to prevent the locking element 5 from being plugged onto the sealing plunger 4 and thus the mixing rod 2 to be unlocked inadvertently. The spacer 6 comprises a handle 8 by means of which it can be pulled out between the sealing plunger 4 and the locking element 5, even if the feed plunger is arranged in the cartridge.

FIG. 2 shows a schematic cross-sectional view through a device according to the invention along a sectional plane A-A in FIG. 1, and FIG. 3 shows a schematic cross-sectional view through a device according to the invention perpendicular to that of FIG. 2 along a sectional plane B-B in FIG. 1. The cartridge 9, or the cartridge wall 9 as the case may be, is drawn in the FIGS. 2 and 3, whereby the feed plunger is situated in the starting position.

Two recesses are arranged on a cylinder-shaped external wall of the sterilisation plunger 3 and extend on the top of the sterilisation plunger 3 approximately from the middle of the sterilisation plunger 3 outwards out of the cartridge 9. One snap-in element 10 each is arranged on the outside between the two slits, whereby the width of the recesses is slightly larger than the width of the snap-in means 10. This means that the snap-in means 10 are each situated on a strip 12 that is connected to the external wall of the sterilisation plunger 3 only on its side facing the bottom of the sterilisation plunger 3. Said strip 12 extends to beyond the upper edge of the sterilisation plunger 3 and is designed as a grasping part 14 that can be operated by hand from outside and projects from the inside of the cartridge in the assembled starting position.

Two depressions for accommodation of the snap-in means 10 are arranged as counter-snap-in means in the internal cartridge walls 9. The grasping part 14 can be pressed in the direction of the longitudinal axis of the sterilisation plunger 3. In this context, the snap-in means 10 moves away from the inside of the cartridge 9 and out of the depressions of the internal cartridge wall 9 and the locking is thus detached. Theoretically, the sterilisation plunger 3 can be structured to comprise just one snap-in means and one grasping part for actuation of the snap-in means, but it is less easy to operate in this case, since two grasping parts 14 are to operate with two fingers.

The sealing plunger 4 has two recesses on the outside for accommodation of the grasping parts 14, or of the strips 12 of the snap-in means 10 of the sterilisation plunger 3 as the case may be. The recesses accommodate the strip 12 when these are pressed together towards the mixing rod 2 in order to detach the snap-in means 10.

The sealing plunger 4 comprises a vacuum connector 16. It is particularly preferred according to the invention that the sealing plunger 4 can contain a non-return valve (not shown) connected to the vacuum connector 16. In this context, the non-return valve is designed such that a gas flow is feasible from the underside of the sealing plunger 4 towards the vacuum connector 16 only and no gas flow can proceed from the vacuum connector 16 towards the underside of the sealing plunger 4. The non-return valve can be designed as a ball valve. The non-return valve is particularly important when the cement dough is pressed out by applying pressurised gas to the plunger system 3, 4, 5 to prevent the ingress of pressurised gas into a cement dough on the inside of the cartridge 9.

The sealing plunger 4 comprises a multitude of tiltable clamping jaws 18 (not shown in FIG. 1) which can be pressed against the mixing rod 2 by their end facing away from the bottom of the sealing plunger 4, by tilting in the direction of the longitudinal axis of the mixing rod 2. The clamping jaws 18 are formed through an axially slitted cylinder that is situated on the top of the sealing plunger 4 and surrounds the mixing rod 2. Said cylinder comprises slits for this purpose that extend from the upper edge of the cylinder to the top of the sealing plunger 4. Strips are thus formed that represent clamping jaws 18 that can be tilted towards the mixing rod 2.

Alternatively, though not shown in FIGS. 1 to 6, the locking element 5 also can contain at least one tiltable clamping jaw, which can be pressed against the mixing rod 2 by its end facing away from the pivot point of the clamping jaw, by tilting in the direction of the longitudinal axis of the mixing rod 2. Said clamping jaws can be formed by an axially slitted cylinder that is arranged on the underside of the locking element 5, which faces the top of the sealing plunger 4.

The locking element 5 can contain at least one element capable of elastic deformation which presses the at least one clamping jaw 18 against the mixing rod 2 after sliding together or plugging on a locking element 5 onto the sealing plunger. The locking element 5, the sealing plunger 4, and the sterilisation plunger 3 each contain a recess in their middle axis to allow same to be axially moved on the mixing rod 2. Slits extend radially from the recess of the locking element 5. The slits form trapezoidal strips which can be deformed elastically in axial direction if suitable plastic materials are used. It is feasible just as well that the locking element 5 contains just a simple plastic cylinder for pressing-on the clamping jaws. This utilises only the elasticity of the plastic material that is used.

Moreover, the invention can provide the sealing plunger 4 to contain at least one element capable of elastic deformation, which, after sliding together or plugging the locking element 5 onto the sealing plunger 4, presses the at least one clamping jaw 18 against the mixing rod 2.

The sealing plunger 4 can be plugged onto the sterilisation plunger 3 which forms a two-part plunger. After the cement is mixed, the locking element 5 is plugged or slid onto the two-part plunger made up by the sealing plunger 4 and the sterilisation plunger 3 which forms a three-part feed plunger. The three-part plunger system surrounds the mixing rod 2.

An advantageous development of the device has a manually removable spacer 6 arranged as securing element 6 between the locking element 5 and the sealing plunger 4, to the effect that the spacer prevents the locking element 5 and the sealing plunger 4 from being slid together or plugged together inadvertently.

In this context, the invention can provide the locking element 5 to be connectible to the sealing plunger 4 by means of being slid together or plugging onto the sealing plunger 4 in a positive fit-like or non-positive fit-like manner in appropriate manner such that the at least one clamping jaw 18 is pressed against the mixing rod 2. This affixes the mixing rod 2 and blocks it with respect to any vacuum-elicited pull towards the inside of the cartridge.

The locking element 5 is connected to the sealing plunger 4 through four snap-in elements 20 in non-detachable manner. The locking element 5 can thus no longer be detached from the sealing plunger 4 such that the mixing rod 2 is safely secured against being shifted due to the action of a vacuum.

The spacer 6 comprises two lateral recesses for the grasping parts 14, or the strips 12 as the case may be, of the sterilisation plunger 3.

It is advantageous for the function of the device that the three-part plunger system 3, 4, 5 can be shifted axially into the mixing cylinder, or into the cartridge 9 as the case may be, by means of vacuum action after manual unlocking in order to move a bone cement, which has been prepared from the bone cement powder by mixing, and the monomer towards a cartridge head. The bone cement dough formed can thus be collected in a vacuum while largely avoiding gas inclusions.

According to the invention, a dispensing opening of the cartridge 9 preferably possesses a connecting means. A connecting thread is particularly well-suited for this purpose. The connecting thread can be used to screw-retain a dispensing tube that is used to introduce the mixed bone cement dough into bone cavities, for example the proximal femur, for fixation of articular endoprostheses.

According to a particularly preferred development of the invention, the mixing rod 2 comprises a predetermined breakage site 22, whereby it is particularly preferred that the predetermined breakage site 22 of the mixing rod 2 is arranged appropriately such that it is covered by the spacer 6 or by the locking element 5 because of the spacer 6, when the mixing element 1 is pulled onto the underside of the sterilisation plunger 3 by means of the mixing rod 2. The mixing rod 2 can thus be prevented from prematurely breaking off as long as the spacer 6 is situated as securing element between the sealing plunger 4 and the locking element 5, since the predetermined breakage site 22 is covered by the locking element 5. This largely prevents a step of faulty operation.

A seal 24 is arranged circumferentially about the outside of the sterilisation plunger 3 and seals the sterilisation plunger 3 with respect to the internal cartridge wall. Likewise, a seal 26 is arranged about the outside of the sealing plunger 4 and seals the sealing plunger 4 with respect to the sterilisation plunger 3, when same is assembled. The seals 24, 26 consist of rubber and are arranged in a circumferential groove about the sterilisation plunger 3 and the sealing plunger 4, respectively.

The sterilisation plunger 3 comprises, on its underside, a gas-permeable porous disc 28. The porous disc 28 is supported by a ribbing 30 of the sterilisation plunger 3.

The vacuum connector 16 terminates in a circumferential gas channel 32 that is provided in the sealing plunger 4.

FIG. 7 shows a schematic side view of the feed plunger having securing element 6 and non-locked mixing rod 2, and FIG. 8 shows a schematic side view of the feed plunger having no securing element 6 and having a locked mixing rod 2 in order to illustrate the method according to the invention and the workings of devices according to the invention.

FIGS. 7 and 8 show only two parts of the feed plunger, namely the sealing plunger 4 and the locking element 5. These are structured as in the exemplary embodiment shown in FIGS. 1 to 6. The sterilisation plunger 3 is not shown in FIGS. 7 and 8 and completes the feed plunger on its outside. A circumferential seal 26 seals the sealing plunger 4 with respect to a cylindrical internal wall of the sterilisation plunger (not shown in FIGS. 7 and 8). The mixing rod 2 extends through a lead-through on the inside of the sealing plunger 4 and locking element 5 and brackets the mixing element 1.

In the situation depicted in FIG. 7, the spacer 6 is also arranged between the sealing plunger 4 and the locking element 5. The snap-in elements 20 of the locking element 5 engage recesses in the sealing plunger 4 dedicated to this purpose. After the cartridge content is mixed by the mixing element 1, the mixing rod 2 is pulled upwards until the mixing element 1 touches against the sterilisation plunger 3. Since the sterilisation plunger 3 is not shown in FIGS. 7 and 8, there is a clearance with respect to the sealing plunger 4 in this position.

Subsequently, the spacer 6 is pulled out by the handle 8. For this purpose, the spacer 6 is provided with a slit, in which the mixing rod 2 is arranged and whose width is equal to or slightly larger than the diameter of the mixing rod 2. If the spacer 6 consists of an elastic or easily deformable material, the slit can, including in regions thereof, just as well be narrower than the diameter of the mixing rod 2.

Then the locking element 5 is slid or plugged onto the sealing plunger 4. This exposes the predetermined breakage site 22 of the mixing rod 2. Moreover, the clamping jaws 18 are pressed onto the mixing rod 2 and the mixing rod 2 is thus being locked in place. This situation is shown in FIG. 8. In this context, the snap-in means 20 of the locking element 5 slip from the original recesses and slip into recesses in the sealing plunger 4 that are arranged more deeply. The snap-in means 20 are bevelled on their outside such that the locking element 5 can move downwards into the sealing plunger 4, but the locking element 5 cannot be pulled out of the sealing plunger 4.

FIG. 9 shows a schematic cross-sectional view of the structure of a bone cement system according to the invention having a cartridge 80. A locked feed plunger 81 is arranged in the cartridge 80 and is arranged such as to be mobile on the inside of the cartridge 80 in the longitudinal direction of the cartridge 80 in its unlocked state. The feed plunger 81 comprises a seal 82 and a stripping lip 84 that surround the feed plunger 81 along its entire circumference. Two locking devices 85 are arranged on the feed plunger 81 on the top of the feed plunger 81. A vacuum connector 87 through which the inside of the cartridge 80 can be evacuated is provided on the top of the feed plunger 81.

A mixing rod 89 having a predetermined breakage site 88 extends through a guiding sleeve 90 through the feed plunger 81. A mixing vane 91 is arranged on the mixing rod 89 on the inside of the cartridge 80. The mixing rod 89 is supported like in a bearing in the feed plunger 81 such that it can rotate such that the mixing vane 91 can rotate in the cartridge 80 and can be shifted in longitudinal direction (up and down in FIG. 9). The inside of the cartridge 80 is bordered by a cylindrical cartridge wall 92 such that a cylindrical hollow space is formed on the inside of the cartridge 80, which, aside from the lower funnel-shaped part of the internal space (in the lower region of the internal cartridge space in FIG. 9) forms the inside of the cartridge 80.

A grasp 95 is arranged on the upper end of the mixing rod 89 and can be used to operate the mixing rod 89 manually or, just as well, through a motor. On the side of the cartridge 80 that is opposite to the locked feed plunger 81, the internal cartridge space terminates in a dispensing opening 96 through which a material present in the cartridge 80 can be squeezed out using the unlocked feed plunger 81. In the region of the dispensing opening 96, the cartridge 80 has an external thread 97 for connecting the cartridge 80 to a tubing 98 of a carrier 99. For this purpose, the cartridge 80 is screwed into an internal thread of the carrier 99.

An ampoule 100 containing a monomer liquid is arranged in a container 102 on the other side of the carrier 99. The ampoule 100 can be opened through an opening mechanism 104 that shears off the head of the ampoule 100.

The cartridge 80 is filled to approx. ⅔ level with a bone cement powder. For sterilisation of the content, the inside of the cartridge 80 is initially evacuated through the vacuum connector 87. Subsequently, a sterilising gas, such as, for example, ethylene oxide, is guided into the cartridge 80. After sufficient time for sterilisation of the content of cartridge 80 has elapsed, the ethylene oxide is removed again with a pump.

The opening mechanism 104 is then used to open the ampoule 100 and the monomer liquid flows into the tubing 98. Owing to the negative pressure on the inside of the cartridge 80, the monomer liquid is aspirated into the cartridge 80 where it mixes with the cement powder. The mixing rod 89 and the mixing vane 91 can be used to mix the monomer liquid and the cement powder. Owing to the vacuum, no unwanted air inclusions are generated in the cement mixture that is being produced. After the mixing process, the mixing rod 89 is pulled upwards to the limit stop of the mixing vane 91 on the feed plunger 81 and the clamping jaws 78 are pressed onto the mixing rod 89 by means of the locking mechanism 79. In this context, the mandrels of the clamping jaws 78 are pressed into the mixing rod 89 below the predetermined breakage site 88 and affix it additionally to the contact surface of the clamping jaws 78 being pressed on. Subsequently, the mixing rod 89 can be broken off at the predetermined breakage site 88, but remains affixed by means of the locked clamping jaws 78.

Subsequently, the feed plunger 81 is being manually unlocked at the locking devices 85. Since the pressure inside the cartridge 80 is lower than in its surroundings, the feed plunger 81 including the clamping jaws 78 and locking mechanism 79 is drawn along with the mixing rod 89 into the inside of the cartridge 80. The cartridge 80 is opened on its front, for example by operating a valve (not shown), or the cartridge 80 is unscrewed from the carrier 99. Pushing-in the feed plunger 81 then causes the cement mixture to be squeezed out of the inside of the feed plunger 81 through the dispensing opening 96. The feed plunger 89 can be conveyed into the cartridge 80 also by means of a pressureised gas being applied to the top of the feed plunger 81. For this purpose, a non-return valve (not shown) is arranged in the vacuum connector 87 and prevents ingress of the pressurised gas into the inside of the cartridge, i.e. into the cement mixture inside the cartridge 80.

A dispensing tube can be screwed onto the thread 97 such that the bone cement can easily be applied at the desired site.

The bone cement system according to the invention having the above-described device according to the invention for mixing and dispensing bone cement is therefore composed of a reservoir element 102 for a binding agent, in particular a monomer, and a base element 99, whereby the base element 99 stores the device having the cartridge 80 and the reservoir element 102. Said bone cement system and the device according to the invention jointly form a closed prepac system, in which not only the cement powder, but also the monomer, is already present in separate compartments in the bone cement system before the cement components are mixed, whereby the monomer liquid that is present is transferred into the cement powder only right before the mixing process.

For this purpose, the base element 99 contains the internal thread 97 as coupling means for a non-positive fit-like and/or positive fit-like connection to the device, in particular to a dispensing opening in the device.

The reservoir element 102 contains the container 100 for the binding agent, in particular the monomer. Whereby the container 100 preferably is a glass container. Glass ampoules, in particular, are conceivable as glass containers. Alternatively, the container 100 can be provided in the form of a tubular bag or side-sealed bag. Said bags can be made from diffusion-inhibiting multi-ply plastic films or, just as well, from aluminium-based composite foils.

According to the invention, the reservoir element 102 can comprise a valve means (not shown) in order to control and/or trigger an outflow of the monomer from the container 100. Said valve element can, in particular, be designed as element 104 for the opening of glass ampoules. Furthermore, the valve element can also be well-suited for the opening of tubular bags or side-sealed bags provided tubular bags or side-sealed bags are used or are to be usable as container 100 for the monomer.

The base element 99 comprises a tubing means 98, whereby the monomer flows from the reservoir container 102 through the tubing means into the device, in particular into the cartridge 80 provided the container 100 was earlier opened by the opening mechanism and/or the valve means 104. It is particularly advantageous in this context to have the monomer be aspirated through the tubing means 98 into the cartridge 80 through the action of a vacuum.

The features of the invention disclosed in the preceding description and in the claims, figures, and exemplary embodiments, can be essential for the implementation of the various embodiments of the invention both alone and in any combination.

LIST OF REFERENCE NUMBERS

1 Mixing element
2 Mixing rod
3 Sterilisation plunger
4 Sealing plunger
5 Locking element
6 Spacer/securing element
8 Grasp
9 Cartridge
10 Snap-in means
12 Strip
14 Grasping part
16 Vacuum connector
18 Clamping jaw
20 Snap-in means
22 Predetermined breakage site
24, 26 Seal
28 Porous disc
30 Ribbing
32 Gas channel
78 Clamping jaw including mandrel
79 Locking element
80 Cartridge
81 Feed plunger
82 Seal
83 Porous disc
84 Stripping lip
85 Locking device
87 Vacuum connector
88 Predetermined breakage site
89 Mixing rod
90 Guide bushing
91 Mixing element/mixing vane
92 Cartridge wall
95 Grasp
96 Dispensing opening
97 Thread
98 Tubing
99 Support/base element
100 Ampoule
102 Container/reservoir element
104 Opening mechanism

The invention claimed is:

1. A device for mixing and dispensing a pasty mass, the device comprising a cartridge having a mixing element and a feed plunger arranged therein, whereby the feed plunger, being in a starting position, is arranged in a region of a first cartridge end of the cartridge, wherein the mixing element is arranged on a mixing rod, wherein the mixing rod extends through the feed plunger into an inside of the cartridge, wherein the mixing rod, the feed plunger and the cartridge together form a tight connection that seals the cartridge inside of the device with respect to an exterior, wherein the feed plunger is arranged such as to be axially mobile on the mixing rod and in the cartridge, wherein the feed plunger comprises a scaling plunger arranged such that the sealing plunger is axially shiftable on the mixing rod and has clamping jaws arranged thereon, wherein the clamping jaws surround the mixing rod such that ends of the clamping jaws are pressable or tiltable against the mixing rod, by means of a locking element, such that the mixing rod is no longer shiftable with respect to the feed plunger, wherein the clamping jaws are pressable against the mixing rod by the ends that face away from a bottom of the sealing plunger, by tilting in the direction of the longitudinal axis of the mixing rod, wherein the clamping jaws are formed through an axially slitted cylinder situated on a top of the sealing plunger and surrounding the mixing rod, wherein the bottom of sealing plunger is located opposite with respect to the top of the sealing plunger, and further wherein the axially slitted cylinder comprises slits that extend from an upper edge of the axially slitted cylinder to the top of sealing plunger.

2. The device according to claim 1, wherein the locking element is a part of the feed plunger and is shiftable on the mixing rod in axial direction with respect to a remaining portion of the feed plunger and, upon the locking element being slid or plugged together with the remaining portion of the feed plunger, presses the ends of the clamping jaws onto the mixing rod such that the mixing rod is no longer shiftable with respect to the feed plunger.

3. The device according to claim 2, wherein a manually-removable spacer is arranged as a securing element between the locking element and the remaining portion of the feed plunger and prevents the locking element and the remaining portion of the feed plunger from being slid together or plugged together.

4. The device according to claim 1, wherein the locking element is arranged on an outward-facing end of the feed plunger.

5. The device according to claim 1, wherein the feed plunger comprises, on an end facing the inside of the cartridge, a sterilisation plunger adjacent to which the mixing element is arranged in the cartridge, wherein the sterilisation plunger comprises at least one gas-permeable exchange surface and is connectable to the cartridge by means of at least one detachable snap-in element.

6. The device according to claim 5, wherein the sterilisation plunger and the sealing plunger and/or the locking element, slid together or plugged together, form an at least two-part feed plunger.

7. The device according to claim 6, wherein the sealing plunger can be plugged onto the sterilisation plunger and in that the locking element can be plugged or slid onto the feed plunger part assembled from the sealing plunger and the sterilisation plunger, while forming a three-part feed plunger.

8. The device according to claim 7, wherein the sealing plunger comprises at least one recess on an outside for accommodating a grasping part of the at least one snap-in means of the sterilisation plunger.

9. The device according to claim 7, wherein the three-part feed plunger system is axially shiftable into the cartridge after an unlocking by means of a pressure in order to move a bone cement dough prepared by mixing bone cement powder and a monomer from the inside of the cartridge towards a cartridge head that is arranged on a second end of the cartridge that is opposite from a first end of the cartridge and includes the second opening.

10. The device according to claim 1, wherein the mixing rod comprises a predetermined breakage site, whereby the predetermined breakage site of the mixing rod is arranged such that the predetermined breakage site is covered by a spacer when the mixing element including the mixing rod is pulled to the end of the feed plunger facing into the inside of the cartridge.

11. The device according to claim 10, wherein the feed plunger and/or the sterilisation plunger comprises at least one vacuum connector that provides a connection from outside through the feed plunger into the inside of the cartridge, whereby a non-return valve is arranged in the vacuum connector.

12. The device according to claim 1, wherein the clamping jaws are tiltable and pressable onto the mixing rod, by the ends of the clamping jaws which are tilted ends.

13. The device according to claim 12, wherein the locking element comprises at least one tiltable clamping jaw that is pressable towards mixing rod by an end of the at least one tiltable clamping jaw.

14. The device according to claim 13, wherein the locking element and/or the sealing plunger comprise at least one element capable of elastic deformation which presses the clamping jaws onto the mixing rod after the locking element is slid together or plugged onto the sealing plunger.

15. A bone cement system comprising the device according to claim 1, wherein the system comprises a reservoir element for a binding agent and a base element, whereby the base element stores and connects the device and the reservoir element.

16. The bone cement system according to claim 15, wherein the base element comprises a coupling means for a non-positive fit- or positive fit-like connection to a dispensing opening of the device.

17. The bone cement system according to claim 15, wherein the reservoir element comprises a valve means configured to control and/or trigger an outflow of the binding agent from the reservoir element.

18. The bone cement system according to claim 17, wherein the base element comprises a tubing, wherein the tubing connects the reservoir element to the inside of the cartridge such that the binding agent is flowable from the reservoir element through the tubing into the cartridge.

19. A method for producing a cement mixture having the bone cement system according to claim 15, the method comprising:
   A) providing the cartridge with at least regions of which are filled with a powder;
   D) filling the cartridge with a monomer;
   E) mixing the powder by means of the mixing element;
   F) locking the mixing rod in the feed plunger by means of the clamping jaws; and
   H) dispensing the cement mixture through propelling the feed plunger.

20. The method according to claim 19, further comprising:
   B) filling a sterilising gas through the gas-permeable exchange surface and sterilising the interior space of the cartridge and the powder after step A) and before step D); and by the cartridge being closed by the sterilisation plunger in step A).

21. The method according to claim 20, further comprising:
   C) plugging the sealing plunger into the sterilisation plunger after step B) and before step D).

22. The method according to claim 21, further comprising:

G) breaking-off the mixing rod locked by means of the clamping jaws after step F) and before step H), whereby the mixing rod preferably is broken off at a predetermined breakage site.

23. The method according to claim 19, wherein the mixing rod in step F) is locked by sliding or plugging the locking element onto the sealing plunger, whereby the locking element presses the clamping jaws onto the mixing rod due to the sliding or plugging.

24. The device according to claim 13, wherein the at least one tiltable clamping jaw of the locking element comprises slits extending radially from a recess of the locking element.

25. The device according to claim 24, wherein the at least one tiltable clamping jaw are formed by an axially slitted cylinder arranged on the underside of the locking element, that faces the top of the sealing plunger.

\* \* \* \* \*